(12) United States Patent  
Ericson

(10) Patent No.: US 6,176,142 B1  
(45) Date of Patent: Jan. 23, 2001

(54) COMPOSITE COATED JAW FACES

(75) Inventor: David Ronald Ericson, Cape May Court House, NJ (US)

(73) Assignee: E. I. du Pont de Nemours and Company, Wilmington, DE (US)

( * ) Notice: Under 35 U.S.C. 154(b), the term of this patent shall be extended for 0 days.

(21) Appl. No.: 09/340,416

(22) Filed: Jun. 28, 1999

Related U.S. Application Data

(60) Provisional application No. 60/097,426, filed on Aug. 21, 1998.

(51) Int. Cl.⁷ .................................................. G01N 3/02
(52) U.S. Cl. ............................................................ 73/856
(58) Field of Search ............................ 73/826, 831, 833, 73/856, 860

(56) References Cited

U.S. PATENT DOCUMENTS

| 3,840,255 | * | 10/1974 | Daghe | 285/45 |
| 3,906,619 | * | 9/1975 | Shaffer | 29/517 |
| 4,012,039 | * | 3/1977 | Yerke | 473/568 |
| 4,194,402 | | 3/1980 | De Nicola | 73/859 |
| 5,329,820 | | 7/1994 | McMahon | 73/833 |

* cited by examiner

Primary Examiner—Max Noori

(57) ABSTRACT

Clamp or grip faces used in fiber/fabric tensile testing instruments are coated with an aramid-epoxy composite, thus allowing high-strength fiber/fabric samples to be tested with greater reproducibility at lower applied pressure and without clamp or grip face scarring.

7 Claims, 1 Drawing Sheet

COMPOSITE COATED JAW FACES

This application claims priority benefit from U.S. Provisional Application Ser. No. 60/097,426, filed Aug. 21, 1998.

FIELD OF THE INVENTION

This invention relates to composite coated jaw faces for testing clamps or grips, specifically an improved surface which enables testing at lower clamp pressures and provides higher overall testing accuracy and reproducibility.

TECHNICAL BACKGROUND

The use of constant-rate-of-extension (CRE) tensile testing machines to determine fiber and fabric properties is well known to those skilled in the art. These machines (e.g., those made by the Instron Corporation, Canton, Mass.; MTS Systems Corp., Eden Prairie, Minn.; United Calibration Corp., Huntingdon Beach, Calif.) have clamps or grips which are designed to grasp the ends of the material (fiber, fabric, etc.) to be tested. There are many different types of clamps or grips, and the selection of the one best suited to the testing procedure is described in supplier literature (see for example "Guide to Advanced Materials Testing", Instron Corp., CAT-8701, pp. 131–140) as well as various ASTM methods (see for example ASTM D2261-96).

The clamps are designed to provide enough compressive force to securely hold the ends of the material or fiber to be tested, so that when the sample is stretched or flexed, for example, the ends do not pull out of the clamps nor are they sheared, but rather remain in place. The clamps on the CRE instruments are generally made of steel and other materials and the opposing faces of the clamps are often coated with a resilient material. This material can be comprised of elastomers such as Neoprene® or Adiprene®, for example. This surface is generally about 0.050 inches thick, which helps prevent the sample from being pinched at the clamp to clamp contact edge. However, these clamps do not prevent slippage and damage of materials made from high strength fibers or the fibers themselves, and additional clamp pressure is necessary when testing these materials, sometimes on the order of 500 psi or greater. This added pressure allows the test sample to be pinched at the clamp to clamp contact edge, and the yield/break point is no longer in the center of the testing zone. Additionally, these clamp faces are scarred by the high-strength materials, and must be recoated after relatively few test runs, thus resulting in additional expense and instrument down time.

There are a wide variety of clamp faces and coating materials described in the art, but none which describe the current composite coating. U.S. Pat. No. 4,194,402 describes the use of wedge-shaped clamp faces made of low-friction material such as Teflon®. U.S. Pat. No. 5,329,820 describes the use of "O"-rings of butadiene acrylonitrile rubber as clamp faces.

SUMMARY OF THE INVENTION

The present invention relates to an improvement in a clamp or grip used in a materials testing machine of the type having a pair of grips or clamps, with grip or clamp faces, for gripping two ends of a test specimen, power means for applying loads to said test specimen through said grips, and control means for controlling said power means, the improvement comprising coating said grip or clamp faces with a material comprised of an aramid-epoxy composite. The aramid-epoxy composite may be further comprised of aluminum oxide fiber or other materials to improve friction characteristics, and the aramid material may be spunlace, woven fabric or pulp.

The invention further relates to a process for coating these faces by:

a) mixing an epoxy resin material with an appropriate catalyst material;

b) spreading the catalyzed epoxy resin material onto a sheet of release film;

c) placing aramid material onto the top of the catalyzed epoxy resin material, thereby allowing the epoxy material to soak through said aramid material so that substantially all air voids are removed, and thereby forming an aramid-epoxy composite;

d) placing said clamp faces down on top of the aramid-epoxy composite, said clamp faces having been roughened to provide good adhesion;

e) allowing the aramid-epoxy material to cure and adhere to the clamp faces;

f) removing the coated clamps from the release film;

g) removing the excess aramid-epoxy material from the edges of the clamp faces; and h) roughening the coated clamp faces to provide a matte finish.

This invention also relates to a method for using these coated clamps to test generally high-strength materials at substantially lower clamping pressure, for example 65 psi line pressure as compared to a "house pressure" of 90 psi line pressure.

DETAILS OF THE INVENTION

Figure 1:
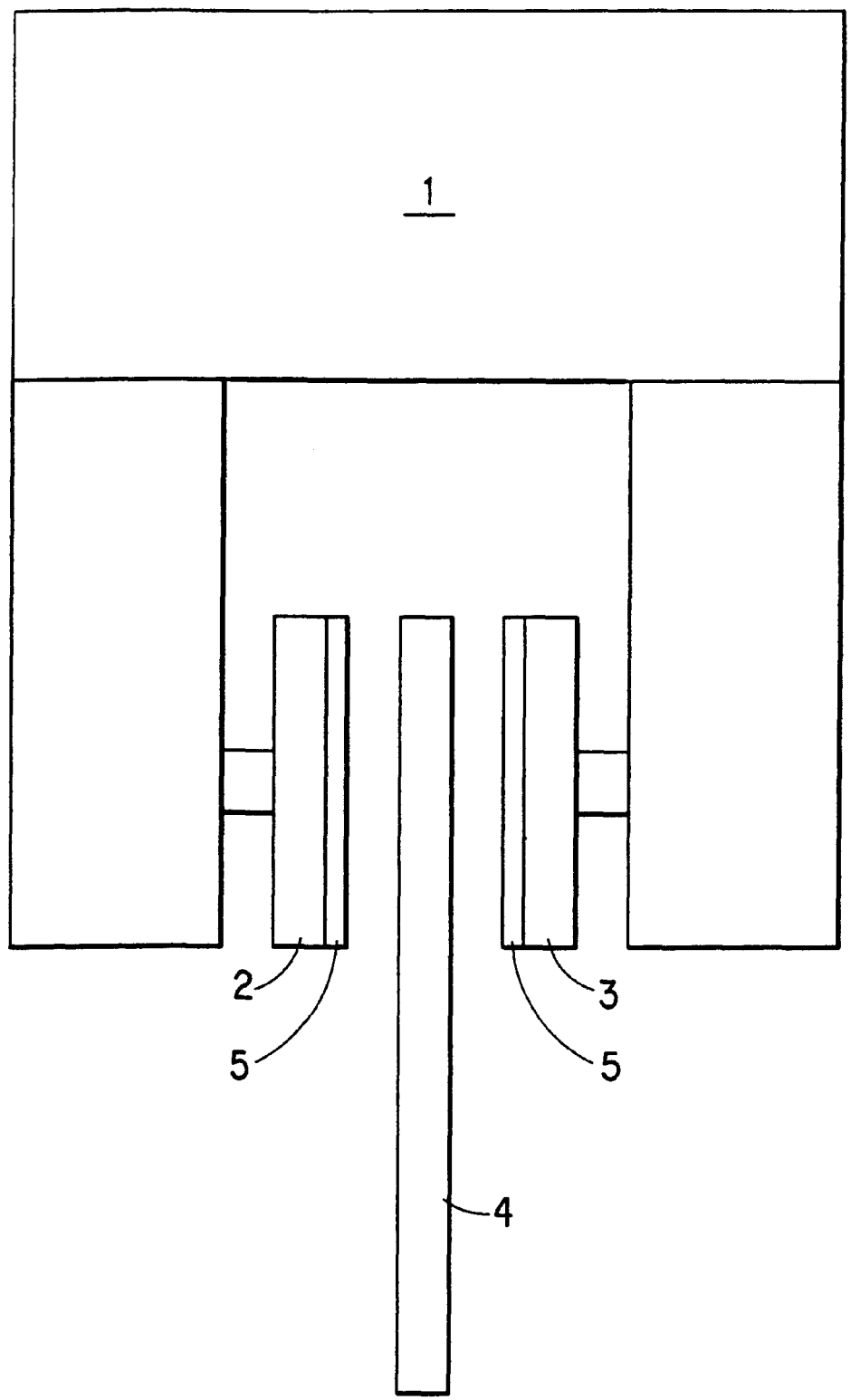
FIG. 1 is a block diagram of a clamp with composite applied to the clamp faces, as described in the details below.

This invention relates to a composite coating which provides an improved surface on clamps or grips for holding, and testing fabric samples. These coated clamps or grips are produced as described below.

Clamp Face Coating Procedure

Steel clamps are obtained from Instron Corporation (such as Series 1120, Canton, Mass.) and the faces were grit-blasted with 65 grit aluminum oxide to provide a matte surface. Alternately, clamps previously coated with a resilient material (e.g., Neoprene® or Adiprene®) or other material can be also subjected to grit-blasting or any other acceptable material to remove the coating material and provide the clean, matte finish necessary.

A sheet of release film (e.g., Tedlar®) is placed onto a flat surface. An epoxy material (Miller-Stevenson 826 or 828) is mixed in approximately a 60:40 volume percent ratio with a catalyst material (with Versamid® 40), and subsequently spread onto the release film. A piece of spunlace Kevlar® (E. I. du Pont de Nemours and Company, Wilmington, Del.) is then placed on top of the catalyzed epoxy material, and allowed to soak into it. Almost all of the air bubbles or voids are forced out of the space between the Kevlar® and the epoxy, thus providing a substantially void-free composite material. While a very small amount of air pockets or voids can be tolerated, the amount should be kept to less than about 1% of the total surface area to provide for this a substantially void-free composite material. Alternatively, a quantity of Kevlar® pulp (type, etc.), for example about 50% by volume of pulp to epoxy material, may be added to the epoxy material rather than using the spunlace material. While this allows more air pockets to form, the composite material produced has performed well in testing. A woven fabric of aramid material could also be used in place of the spunlace or pulp material. Also, any combination of these aramid materials can be used. Aramid materials other than Kevlar® could also be used.

The clamps or grips are then placed face down onto the aramid-epoxy material, and as many clamps as possible can be placed next to one another on one sheet of this material. The aramid-epoxy-clamp configuration is allowed to cure for about 24 hours, or until the aramid-epoxy material have firmly bonded to the clamp faces. The coated clamps were then removed from the release film, the coated clamps are then separated from one another by use of a band-saw or other means, and the excess coating, is removed from the edges of the clamp faces. Because the faces had smooth surfaces resulting from the smoothness of the release film, they are then, preferably, machined to provide a matte finish to increase the contact friction between the fabric being tested and the surface.

A small amount of aluminum oxide or other material can be added to a separate quantity of the epoxy material before the catalyst is added, and the coating procedure is followed as described above. Addition of a small amount of such additives to the epoxy resin, e.g., up to about 10% by volume, may enhance the surface friction characteristics.

Sample Testing

Various samples of woven aramid material were tested according to an E. I. du Pont de Nemours and Company (DuPont) test method TM 1497-93, available from DuPont, Wilmington, Del. 19898. This test method is based on ASTM D2261, "Test Method for Tearing Strength of Woven Fabrics by the Tongue Method", and ASTM 1117, "Methods for Testing Nonwoven Fabrics". Generally, an Instron® Model No. 1120 series is used as outlined in the above-referenced test methods and as further described in the operating manual for the instrument. In summary, a strip of fabric is cut to the appropriate size (e.g., its width must be less than the width of the clamp faces), and the ends of the fabric may be optionally coated to provide for improved gripping. The ends are then placed between the clamp faces, the faces brought together pneumatically until the ends are firmly held. The sample is then tested, for example stretched, torn, stressed or ruptured until a break is detected by the instrument, and the value recorded.

It has been found that substantially less pressure need be applied to the clamps to hold the sample ends in place when the clamp surfaces are coated with the composite herein than with clamps that do not have that coating. With clamps coated with the prior resilient material, pressures of about 90 psi line pressure were required to firmly hold the samples in place while the tests were being performed. Using the present coated clamps, the pressure is reduced to about 60 psi for the same samples. The lower pressure allows the sample to yield/break at a point within the preferred test area (approximately midway between the top and bottom clamp edges), and not yield/break at the point where the opposing clamp edges meet. Additionally, because the pressure used is closer to the center of the recommended range of pressure, the reproducibility of the test is improved.

Another concern related to the use of the clamps coated with a resilient material is the scarring of the clamp faces, which results from high strength materials cutting into the resilient surface as they are clamped and drawn apart by the instrument. After only a few test runs, the resilient material has to be stripped mechanically, generally by grit-blasting, from the clamp face surface, and a new layer applied to each clamp face individually. This is a costly process in terms of material and instrument downtime. The clamps coated by the present invention show no scarring visually or microscopically, even after over 100 test runs, so that the need for recoating will be a rare event. Further, when the clamps are coated by the method described above, the cost per clamp is greatly reduced.

Samples of various materials have been tested using clamps coated with the material described above, including Kevlar® fabric, Cordura® fabric, nylon and polyester. Although most of these materials are considered "high strength" and therefore require the use of relatively high pressure to close the clamps on the instrument, it is expected that any fiber or fabric sample can be tested using these clamps at appropriate clamp pressures for that fiber or fabric.

DETAILED DESCRIPTION OF THE DRAWING

FIG. 1 shows clamp body (1), housing clamp faces (2) and (3) and shown test Specimen (4). Pressure is applied at clamp faces (2) and (3) to hold Specimen (4) in place. Composite is applied at clamp faces (5).

EXAMPLES

The method for coating the faces is described as follows:

Materials

Miller Stephenson Epon 828 epoxy resin
Miller Stephenson Versamid 140 catalyzing agent
DuPont Tedlar® release film
Plastic beaker 500 ml for mixing
Wooden tongue depressors for mixing
DuPont Kevlar® spun lace 2 oz/yd
Clamp faces for grips (oxide blasted w 65 grit alum oxide at 65 psi 2 to 3 passes Procedure A piece of release film was cut to approximate size of 12×12". A batch of resin-catalyst was mixed at 60/40 ratio resin to catalyst. After being thoroughly mixed, the resin and catalyst mixture was poured onto a sheet of film and spread evenly to form a "puddle" about the size of a piece of spunlace Kevlar®). The spunlace Kevlar® was then placed onto the resin which diffused into the spunlace Kevlar®. Once this process was complete, the clamp faces were laid very carefully onto the wetted material. There was no pressure applied to the faces. These were allowed to sit 24 hours so the resin system achieved cure. This process took approximately 40 minutes for a set of 8 faces.

The cured "plaque" was then taken to a cutting shop where it was cut into segments containing the individual faces. The excess composite was cut away and the edges of each face was trimmed and sanded to the edge of the face. The clamp faces then were subjected to grit blasting with 65 grit aluminum oxide to slightly roughen the surface. This completed the application of composite material to a clamp face.

Testing

The clamp faces were placed into their respective grips and line pressure was set at max. During the ensuring process, it was realized that line pressure could be reduced from the maximum of about (90 psi) to 65 psi and still hold specimens while achieving a gage failure.

The traditional method typically caused damage to specimens as well as damaged the surfaces of clamp faces. Of particular note was the fact that fiber particulate imbedded in the damaged surface and further exacerbated the slippage and/or damage problem. This series of fabrics that were tested with the new faces reflected data that was very consistent as well showing expected load values. Achieving gage failure in a given test of this type represents the ideal failure mode. It was the opinion of the testing technician that this was one of the most successful series of tests she had seen when testing the more robust Kevlar® fabrics.

Data

The nominal maximum loads were on the order of 1000 lbs. with the above conditions. The fabrics were style 270 Kevlar® ballistic items that were subjected to various treatments such as scoured, greige or treated with "finish".

What is claimed is:

1. In a materials testing machine of the type having a pair of clamps for gripping two ends of a test specimen, power means for applying loads to said test specimen through said clamps, and control means for controlling said power means, an improvement comprising coating the faces of each of said clamps with a material comprised of an aramid-epoxy composite, wherein the composite material is applied to the clamp faces by:
   a) mixing an epoxy resin material with an appropriate catalyst material;
   b) spreading the catalyzed epoxy resin material onto a sheet of release film;
   c) placing aramid material onto the top of the catalyzed epoxy resin material, thereby allowing the epoxy material to soak through said aramid material so that substantially all air voids are removed, and thereby forming an aramid-epoxy composite;
   d) placing said clamp faces down on top of the aramid-epoxy composite, said clamp faces having been first roughened to provide good adhesion;
   e) allowing the aramid-epoxy material to cure and adhere to the clamp faces;
   f) removing the coated clamps from the release film;
   g) removing the excess aramid-epoxy material from the edges of the clamp faces; and
   h) roughening the coated clamp faces to provide a matte finish, so that the contact friction between the test specimen and the clamp face surface is increased.

2. The materials testing machine of claim 1, wherein the aramid-epoxy composite coating on said clamp faces allows increased contact friction between the test specimen and the clamp faces.

3. The machine as recited in claim 1, wherein said aramid-epoxy composite material is further comprised of aluminum oxide.

4. The machine as recited in claim 1, wherein said aramid material is spunlace.

5. The machine as recited in claim 1, wherein said aramid material is woven fabric.

6. The machine as recited in claim 1, wherein said aramid material is pulp.

7. A method of testing materials using a materials testing machine of the type having a pair of clamps for gripping two ends of a test specimen, power means for applying loads to said test specimen through said clamps, and control means for controlling said power means, an improvement comprising coating the faces of each of said clamps with a material comprised of an aramid-epoxy composite comprising the steps of:
   (a) cutting a test specimen to a size whereby its width is less than the width of the clamp faces;
   (b) optionally coating ends of the sample strip to provide for improved gripping;
   (c) placing said ends between the clamp faces;
   (d) bringing said faces together until the ends are firmly held; and
   (e) operating said machine so that the sample is tested until a break is recorded by the machine, wherein the power means for applying loads to the test specimen is reduced by about 10–30% as compared to grips that do not have aramid-epoxy composite coating as determined by pressure measurements.

* * * * *